(12) United States Patent
Molenda

(10) Patent No.: US 7,268,105 B2
(45) Date of Patent: Sep. 11, 2007

(54) SHAMPOO COMPOSITION COMPRISING A MIXTURE OF GLYCERYL ESTERS

(75) Inventor: Michael Molenda, Frankfurt (DE)

(73) Assignee: KPSS-Kao Professional Salon Services GmbH, Darmstadt (DE)

(*) Notice: Subject to any disclaimer, the term of this patent is extended or adjusted under 35 U.S.C. 154(b) by 0 days.

(21) Appl. No.: 11/302,773

(22) Filed: Dec. 14, 2005

(65) Prior Publication Data

US 2006/0135382 A1 Jun. 22, 2006

(30) Foreign Application Priority Data

Dec. 16, 2004 (EP) ................... 04029775

(51) Int. Cl.
*C11D 1/825* (2006.01)
(52) U.S. Cl. ............... 510/128; 510/119; 510/130; 510/155; 510/253; 510/289; 510/340; 510/356; 510/413; 510/421; 510/422
(58) Field of Classification Search ........... 510/119, 510/130, 155, 253, 289, 340, 356, 413, 421, 510/422
See application file for complete search history.

(56) References Cited

U.S. PATENT DOCUMENTS

| | | | | | |
|---|---|---|---|---|---|
| 5,635,461 | A | * | 6/1997 | Onitsuka et al. | 510/126 |
| 5,696,069 | A | * | 12/1997 | Ito et al. | 510/123 |
| 5,756,077 | A | * | 5/1998 | Syed et al. | 424/70.13 |
| 5,792,737 | A | * | 8/1998 | Gruning et al. | 510/126 |
| 6,046,145 | A | * | 4/2000 | Santora et al. | 510/121 |
| 6,494,920 | B1 | * | 12/2002 | Weuthen et al. | 8/137 |
| 2004/0136940 | A1 | * | 7/2004 | Lazarowitz | 424/70.13 |
| 2004/0241112 | A1 | * | 12/2004 | Evison et al. | 424/59 |
| 2005/0000035 | A1 | * | 1/2005 | Chan et al. | 8/405 |

FOREIGN PATENT DOCUMENTS

| | | |
|---|---|---|
| DE | 299 10 160 U1 | 11/2000 |
| WO | WO 2004/030654 A1 | 4/2004 |

* cited by examiner

*Primary Examiner*—Charles Boyer
(74) *Attorney, Agent, or Firm*—Norris McLaughlin & Marcus PA

(57) ABSTRACT

The present invention is related to thickening shampoo compositions and its long-term stability.

17 Claims, No Drawings

SHAMPOO COMPOSITION COMPRISING A MIXTURE OF GLYCERYL ESTERS

The present invention is related to thickening shampoo compositions and its long-term stability.

Liquid thickened shampoo compositions have been know on the market for many decades. For achieving certain level of consistency various organic and inorganic compounds have been used. One of the well know thickener for shampoo compositions based on anionic surfactants is salt, sodium chloride. Organic ones can be polymeric such as acrylate polymers or of other structures.

In practice one of the problems for formulators is, first of all, thickening cleansing compositions and furthermore, secondly keeping the viscosity of the shampoo without any major change. It should be noted that the consistency of cleansing products plays an important role in its perception.

For compositions having slightly acidic pH values, above 4.5 or more precisely 5.0, it seems that the problem is solved, or no major problems are observed. However, problems have been encountered in thickening and stabilizing recently developed acidic shampoos, i.e. thickening is not as easy as the normal shampoos and furthermore its stability is not given when for example thickened with sodium chloride or any other well known thickening compound.

Recently it has surprisingly been found out that using two of the known organic thickening compounds it has been possible to thicken the shampoo compositions having pH values below 4.5 and their consistency have also found interestingly to be stable during their shelf life.

Accordingly, the present invention is on the shampoo composition comprising at least one surfactant selected from anionic, nonionic, amphoteric and/or zwitterionic ones and having a pH value below 4.5 and comprises further at least one compound presented with the general formula

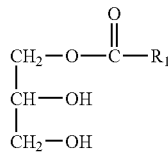

where $R_1$ is a saturated or unsaturated, branched or not alkyl chain with 9 to 19 C atoms as the first thickener compound, and at least one compound with the general formula

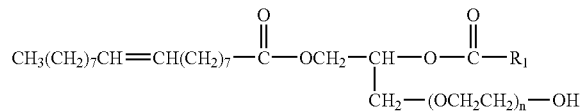

where $R_1$ is same as above and n is between 10 to 30 as the second thickener compound.

In principal it is also possible to thicken conventional shampoo compositions other than those of below pH 4.5 with the thickener combination and those compositions show also good stability. Therefore the pH range of the shampoo compositions is in principal in the range of 2 to 7 and preferably 2 to 4.5, more preferably 2.5 to 4.0, most preferably 2.9 to 3.8.

Examples to the thickening compounds of the one first mentioned above are glyceryl laurate, myristate, stearate, oleate, stearate, palmitate, palmitooleate, cocoate, linoloate. The most preferred compound is the glyceryl laurate, which is sold under the trade name Antil HS 60 by Goldschmidt. The compound is present in the compositions at a concentration from 0.1 to 2.5%, preferably from 0.1 to 2% more preferably from 0.15 to 2% and most preferably from 0.2 to 1.5% by weight calculated to total composition.

The examples to the second compound are PEG 18 glyceryl oleate/cocoate etc. The most preferred one is PEG 18 glyceryl oleate/cocoate wherein in the formula n is equal to 18 and R is is a fatty acyl chain derived from coconut oil. The compound is present in the compositions at a concentration from 0.1 to 2.5%, preferably from 0.1 to 2% more preferably from 0.25 to 2% and most preferably from 0.5 to 1.5% by weight calculated to total composition.

It has also been observed that the mixing ratio of the both components may be important for obtaining a stably thickened personal cleansing composition. The ratio of the component 1 (glyceryl fatty acyl ester) to the second one (ethoxylated di acyl ester) is between 5 to 1 to 1 to 5, preferably 3 to 1 to 1 to 3 and more preferably 2 to 1 to 1 to 2 and the most promising results have been obtained with 1 to 1 mixtures by weight.

EP 1174112 discloses hair cosmetic compositions comprising organic acid, organic solvent, cationic surfactant and higher alcohol and having pH in the range of 2 to 6 for improving hair shine. Additionally, WO 2004/047777 discloses leave-in compositions for hair comprising malic and lactic acids and organic solvents for improving shine, setting and touch feeling. Both documents are silent on thickening cleansing compositions with optimum stability.

In principal pH of the compositions can be adjusted with any organic and/or inorganic acids or their mixture. Some of them to mention are phosphoric acid, hydrochloric acid as the inorganic ones and to the organic acids the well known citric acid. However, the best hair conditioning effects is observed with the carboxylic acids and especially those of with hydroxycarboxylic acids and/or dicarboxylic acids. In those cases where selected hydroxycarboxylic acid and/or dicarboxylic acid concentration is not enough to reach the selected pH, other organic and inorganic acids can as well be used to adjust pH to the required value. The hydroxycarboxilic acids useful in the compositions of the present invention are lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid.

Compositions according to invention in principal comprise at least one hydroxycarboxilic acid and/or dicarboxylic acid. Combinations of two or more hydroxycarboxylic acids and/or dicarboxylic acids are also within the scope of the invention. It should be noted that hydroxycarboxylic acid and dicarboxylic acid comprising compositions are also within the scope of the present invention. Especially preferred hydroxyliccarboxylic acids are the lactic and malic acids. Malic acid is also a discarboxy acid. The most preferred hydroxycarboxylic acid and/or dicarboxylic acid is the malic acid.

Total hydroxycarboxylic acid and/or dicarboxylic acid concentration in the composition of the present invention varies in the range form 0.1 to 5% by weight, preferably 0.25 to 3% by weight, more preferably 0.5 to 3% by weight and most preferably 0.75 to 3% by weight. In a preferred embodiment of the invention, the compositions of the present invention comprise at least 0.5% malic acid.

Shampoo compositions of the present invention comprise at least one surfactant selected from anionic, non-ionic and/or amphoteric or zwitterionic surfactants at a concentration range of 1 to 50%, preferably 5 to 40% and more preferably 5 to 30%, and most preferably 5 to 25% by weight, calculated to the total composition.

In an embodiment of the present invention shampoo composition of the present invention, comprises at least one anionic surfactant, and at least one nonionic surfactant. More preferably the compositions comprise at least one anionic, at least one nonionic and at least one amphoteric surfactant.

Anionic surfactants suitable within the scope of the invention are preferably present in an amount from 1 to about 30%, preferably 2 to 20% and most preferably 2-15%, and most preferably 2 to 10% by weight, calculated to the total composition.

These are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

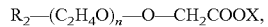

wherein $R_2$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

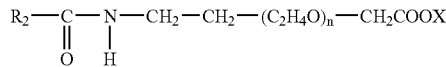

wherein $R_2$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

An overview of the anionic surfactants used in liquid body cleansing compositions can furthermore be found in the monography of K. Schrader, "Grundlagen und Rezepturen der Kosmetika", 2$^{nd}$ Ed.(1989, Hüthig Buchverlag), pp. 595-600 and pp. 683 to 691.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Further surfactants in the shampoo compositions according to the invention are nonionic surfactants in admixture with anionic surfactants.

These are described in Schrader, l.c., on pages 600-601 and pp. 694-695. Especially suited are alkyl polyglucosides of the general formula

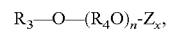

wherein $R_3$ is an alkyl group with 8 to 18 carbon atoms, $R_4$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components are, for example, long-chain fatty acid mono- and dialkanolamides, such as coco fatty acid monoethanolamide and myristic fatty acid monoethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$", as well as fatty alcohol ethoxylates.

Further suitable nonionic surfactants are amineoxides which may be present in an amount from 0.25% to 5% by weight, calculated to the total composition.

Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylates at a concentration of 0.5 to 10%, preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth"

according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the compositions according to the invention can also contain amphoteric or zwitterionic surfactants, for example in an amount from about 0.5% to about 15%, preferably from about 1% to about 10%, by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

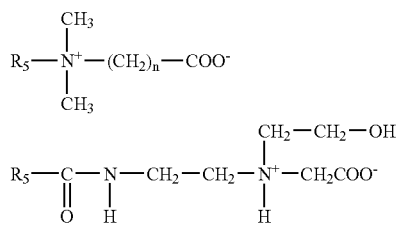

wherein $R_5$ is a $C_8$-$C_{18}$-alkyl group and n is 1 to 3; sulfobetaines of the structure

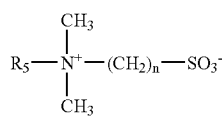

wherein $R_5$ and n are same as above; and amidoalkyl betaines of the structure

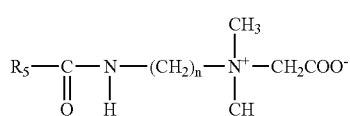

wherein $R_5$ and n are same as above.

The composition of the present invention may comprise hair-conditioning agents. Conditioning agents can be selected from oily substances, non-ionic substances, cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

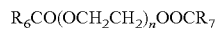

where $R_6$ and $R_7$ are independent from each other saturated, unsaturated or branched or non-branched alkyl chain with 7 to 21 C atoms and n is typically 2-100.

In one of the preferred from of the present invention, personal cleansing compositions comprise at least one cationic polymer as conditioning agent. Suitable cationic polymers are those of best known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

It has further been found out that especially those of cationic cellulose type polymers known as Polymer JR type from Amerchol such as Polyquaternium 10 or cationic guar gum known with trade name Jaguar from Rhône-Poulenc and chemically for example Guar hydroxypropyl trimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, polyquaternium 6 and polyquaternium 7.

The cationic polymers also include the quaternized products of graft polymers from organopolysiloxanes and polyethyl oxazolines described in EP-A 524 612 and EP-A 640 643.

Personal cleansing compositions of the present invention can comprise additionally one or more cationic surfactant(s) as conditioner presented with the general formula

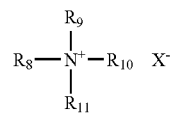

where $R_8$ is a saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has value of 1-4, or $$R_{13}COO(CH_2)_n$$

where $R_{13}$ is saturated or unsaturated, branched or non-branched alkyl chain with 7-21 C atoms and n has value of 1-4, and $R_9$ is hydrogen or unsaturated or saturated, branched or non-branched alkyl chain with 1-4 C atoms or $$R_{12}CONH(CH_2)_n$$

or $$R_{13}COO(CH_2)_n$$

where $R_{12}$, $R_{13}$ and n are same as above.

$R_{10}$ and $R_{11}$ are hydrogen or lower alkyl chain with 1 to 4 carbon atoms, and X is anion such as chloride, bromide, methosulfate.

Typical examples of those ingredients are cetyl trimethly ammonium chloride, stear trimonium chloride, behentrimoinium chloride, stearamidopropyl trimonuim chloride, dioleoylethyl dimethyl ammonium methosulfate, dioleoylethyl hydroxyethylmonium methosulfate.

The compositions according to the invention may also comprise further conditioning substances such as protein hydrolyzates and polypeptides, e.g., keratin hydrolyzates, collagen hydrolyzates of the type "Nutrilan$^R$" or elastin hydrolyzates, as well as also in particular plant protein hydrolyzates, optionally, cationized protein hydrolyzates, e.g., "Gluadin$^R$".

Typical concentration range for any of those conditioners of cationic polymers, silicon oil and derivatives and cationic surfactants can be 0.01-5% by weight, preferably 0.01-3.5% by weight, more preferably 0.05-2.5% and most preferably 0.1-1.5% by weight calculated to the total composition.

Further conditioning additives are hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water-or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in conditioning shampoo composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryl oylethyl betaine and alkyl methacrylates of the type "Yukaformer®", e.g., the butyl methacrylate copolymer "Yukaformer® Am75"; copolymers from monomers containing carboxyl groups and sulfonic groups, e.g., (meth)acrylic acid and itaconic acid, with monomers such as mono- or dialkyl amino alkyl(meth)acrylates or mono- or dialkyl aminoalkyl (meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199, are applicable.

Shampoo composition may comprise organic solvents such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzylalcohol, benzyloxyethanol and polypropylene glycols. Concentration of organic solvents in the shampoo composition should not exceed 5% by weight, preferably in the range of 0.1 to 3%, more preferably 0.5 to 2.5% by weight calculated to total composition.

Solubilizers may be added to the compositions especially when oily substances are chosen as conditioning agents and fragrance oils with highly lipophilic properties. Typical solubilizers may be hydrogenated castor oil known with the trade mark Cremophor RH series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

The compositions of the present invention may comprise active ingredients selected from UV filters, moisturisers, sequestering agents, and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are selected from polycarboxy acids. The preferred one is ethylene diamine tetraacetic acid, EDTA. Typical useful concentration range for sequestering agents is of 0.01-2.5% by weight calculated to the total composition.

The UV filters are those oil and water soluble ones for the purpose of protecting hair colour. In other words, anionic and nonionic, oily or oil soluble, UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher. The amount of the UV-absorber ranges typically from about 0.01% to 2.5%, more preferably from 0.05% to 1% by weight, calculated to the total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol$^R$", "Sedaplant$^R$" and "Hexaplant$^R$". Extracts and the preparation thereof are also described in "Hagers Handbuch der pharmazeutischen Praxis", $4^{th}$ Ed.

The viscosity of the compositions according to the invention is in the range of 1,000 to 20,000 mPa·s at 20° C., preferably 1,000 to 10,000, in particular 1,500 to 8,000 mPa·s at 20° C., measured with Höppler viscosimeter.

It is self-understood that the shampoos according to the invention may comprise other substances customarily used in such compositions such as preservatives, fragrances. A list of such additives can also be found in Schrader, I.c., on pp. 695 to 722.

According to the invention, shampoo composition may comprise direct acting cationic dyestuff. Suitable cationic dyestuffs are in principal those available on the market for hair colouring applications. Some examples to those are: Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

For this purpose, special reference is made to the PCT application WO 95/15144 of Ciba-Geigy AG. The cationic dyestuffs know with their CTFA adopted names Basic Yellow 87, Basic orange 31 and Basic Red 51 are especially preferred ones according to the present invention.

Cationic dyestuffs are included into the compositions of the present invention at a concentration of 0.0001 to 2%, preferably 0.0001 to 1.5% and more preferably 0.0001 to 1% by weight, calculated to total aqueous composition.

Anionic dyes may as well be used in combination with cationic direct dyes at minor quantities. The suitable ones are:

Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

According to the invention, anionic dyes may be included in minor quantities at a concentration around 25%, preferably not more than 10% of the total cationic dye content of the composition.

Additionally, the shampoo compositions of the present invention may comprise neutral dyes (HC dyes), so called nitro dyes in addition to the cationic direct dyes. Concentration of those can typically be in the range of 0.0001 to 1%, preferably 0.0001 to 0.75% and more preferably 0.0001 to 0.5% by weight calculated to total aqueous composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used in combination with cationic direct-acting dyestuffs, for example henna (red or black), alkanna root, laccaic acid, indigo, logwood powder, madder root and rhubarb powder, etc.

The anionic, HC and plant dyes are always used in combination with cationic direct dyes.

The following examples are to illustrate the invention, but not to limit. The compositions according to the invention are prepared by mixing the individual components in water, whereby it is also possible to use pre-mixtures of various ingredients.

EXAMPLE 1

| Shampoo composition | |
|---|---|
| Sodium lauryl ether sulfate | 11.0 (% by wt.) |
| Coco glucoside | 4.0 |
| Cocoamidopropyl betaine | 1.5 |
| Cationic polymer (Polyquaternium-10) | 0.2 |
| Benzylalcohol | 0.25 |
| Perfume, preservative | q.s |
| PEG-60-hydrogenated castor oil | 0.5 |
| PEG-18 Glyceryl cocoate/oleate | 0.8 |
| Glyceryl laurate | 0.8 |
| Malic acid | 1.00 |
| Water | ad 100.0 |

The pH of the composition is 3.6.

For comparative purposes the above composition is preparaed by only using PEG-18 Glyceryl cocoate/oleate (composition A) and Glyceryl laurate (composition B). The initial viscosity values are adjusted by using the respective thickener to that of Example 1. The compositions so obtained were stored for 6 moths at −5° C., room temperature, 40° C. and 50° C. and the viscosity values were measured by using Höppler viscosimetre at 20° C. using the ball no 5. Results are presented in Table I.

TABLE I

Results of stability test - all viscosity values are expressed in mPa · s and measured at 20° C. with Höppler viscosimetre using the ball no 5.

| | Storage Temperature | Start | 1 Month | 3 Months | 6 Months |
|---|---|---|---|---|---|
| Example 1 | −5 | 6925 | 6613 | 7367 | 7487 |
| | RT | | 7157 | 7136 | 7690 |
| | 40 | | 7508 | 7161 | 7813 |
| | 50 | | 7450 | 7646 | 7463 |
| Composition A | −5 | 6795 | 8119 | 5818 | 5418 |
| | RT | | 6260 | 4091 | 2139 |
| | 40 | | 3893 | 1240 | 1925 |
| | 50 | | 2843 | 927 | 1818 |
| Composition B | −5 | 6850 | 7066 | 8119 | 9978 |
| | RT | | 8677 | 10559 | 13668 |
| | 40 | | 11866 | 15100 | 14761 |
| | 50 | | 13102 | 17366 | 15377 |

Example 1 in the table according to the invention and the compositions A and B are comparative compositions as mentioned above. From the results it is clear that the inventive composition is stable in viscosity over the storage period of time and the comparative compositions A and B are not stable, the former is becoming more and more liquid over the storage period and the opposite is true for the latter which becomes more viscosus.

Similar results were observed with following compositions.

EXAMPLE 2

| | |
|---|---|
| Sodium lauryl ether sulfate | 10.0 (% by wt.) |
| Coco glucoside | 5.0 |
| Cocoamidopropyl betaine | 1.5 |
| Cetrimonium chloride | 0.2 |
| Polyquaternium 10 | 0.5 |
| Benzylalcohol | 0.5 |
| Perfume, preservative | q.s |
| PEG-60-hydrogenated castor oil | 0.5 |
| PEG-18 Glyceryl cocoate/oleate | 0.6 |
| Glyceryl laurate | 0.6 |
| Malic acid | 0.7 |
| Lactic acid | 0.3 |
| Basic Red 51 | 0.1 |
| Water | ad 100.0 |

The pH of the composition is 3.3. A shampoo with very good lathering capability and hair conditioning properties especially shine enhancing effect as well as with excellent color enhancing ability (intensive red touch) was obtained. The viscosity was around 5500 mPa·s measured at 20° C. with Höppler viscosimetre. Upon storage of the composition under various storage condition no major change in viscosity was observed.

EXAMPLE 3

| | |
|---|---|
| Sodium lauryl ether sulfate | 10.0 (% by wt.) |
| Coco glucoside | 4.0 |
| Cocoamidopropyl betaine | 2.5 |
| Dimethiconol | 0.2 |
| Polyquaternium 10 | 0.5 |
| Propyleneglycol | 0.5 |
| Perfume, preservative | q.s |
| PEG-60-hydrogenated castor oil | 0.5 |
| PEG-18 Glyceryl cocoate/oleate | 0.8 |
| Glyceryl laurate | 0.5 |
| Malic acid | 0.6 |
| Lactic acid | 0.2 |
| Basic Red 51 | 0.05 |
| Basic Blue 99 | 0.01 |
| Basic Orange 31 | 0.03 |
| Water | ad 100.0 |

The pH of the composition is 3.3. A shampoo with very good lathering capability and hair conditioning properties especially shine enhancing effect as well as with excellent color enhancing ability (intensive brown touch) was obtained. The viscosity was around 6100 mPa·s measured at 20° C. with Höppler viscosimetre. Upon storage of the composition under various storage condition no major change in viscosity was observed.

EXAMPLE 4

| | |
|---|---|
| Sodium lauryl ether sulfate | 11.0 (% by wt.) |
| Coco glucoside | 4.0 |
| Cocoamidopropyl betaine | 1.5 |
| Dimethiconol | 0.2 |
| Polyquaternium 10 | 0.5 |
| Propyleneglycol | 0.5 |
| Perfume, preservative | q.s |
| PEG-60-hydrogenated castor oil | 0.5 |
| PEG-18 Glyceryl cocoate/oleate | 0.4 |
| Glyceryl laurate | 0.4 |
| Malic acid | 0.6 |
| Lactic acid | 0.4 |
| Water | ad 100.0 |

The pH of the composition is 3.1. A shampoo with very good lathering capability and hair conditioning properties especially shine enhancing effect was obtained. The viscosity was around 3100 mPa·s measured at 20° C. with Höppler viscosimetre. Upon storage of the composition under various storage condition no major change in viscosity was observed.

The invention claimed is:

1. Shampoo composition comprising:
   (a) at least one surfactant selected from the group consisting of anionic surfactants, nonionic surfactants, amphoteric surfactants, zwitterionic surfactantants and mixtures thereof;
   (b) a first thickener having the general formula

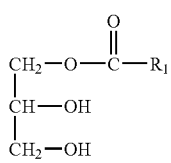

where $R_1$ is a saturated or unsaturated and branched or unbranched alkyl chain having 9 to 19 Carbon atoms; and (c) a second thickener having the general formula

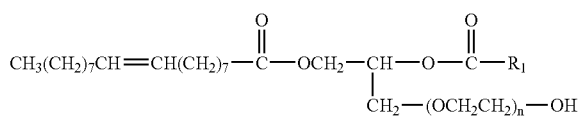

where $R_1$ is a saturated or unsaturated and branched or unbranched alkyl changing having 9 to 19 Carbon atoms and n is a number between 10 and 30,
wherein the ratio of the first thickener to the second thickener in the shampoo composition is in the range of about 1:2 to 5:1.

2. Composition according to claim 1 characterized in that the concentration of surfactant is in the range of 1 to 50% based on the weight of the total composition.

3. Composition according to claim 1 wherein the composition comprises at least one anionic surfactant and at least one non-ionic surfactant.

4. Composition according to claim 3 wherein the composition comprises additionally at least one amphoteric surfactant.

5. Composition according to claim 1 wherein the first thickening compound comprises glyceryl laurate.

6. Composition according to claim 1 wherein the second thickening compound comprises PEG-18 Glyceryl oleate/cocoate.

7. Composition according to claim 1 wherein the composition has a pH in the range of 2 to 7.

8. Composition according to claim 1 wherein the composition has a pH in the range of 2.0 to 4.5.

9. Composition according to claim 1 wherein the composition comprises a hair conditioning compound comprising at least one cationic polymer and/or at least one cationic surfactant.

10. Composition according to claim 1 wherein the composition comprises an acidic compound for adjusting the pH of the composition wherein the acidic compound comprises at least one hydroxycarboxylic acid and/or dicarboxylic acid at a concentration of 0.1 to 5% based on the weight of the total composition.

11. Composition according to claim 10 wherein the composition comprises malic acid and/or lactic acid as the hydroxycarboxylic acid.

12. Composition according to claim 10 wherein the composition comprises hydroxycarboxylic acid at a concentration of 0.5 to 5% by weight with the condition that it comprises malic acid at a concentration of not less than 0.5% based on the weight of the total composition.

13. Composition according to claim 10 wherein the composition comprises only malic acid as a hydroxycarboxylic acid and/or dicarboxylic acid.

14. Composition according to claim 1 wherein the composition comprises additionally at least one direct hair dye.

15. Composition according to claim 1 wherein the composition comprises organic solvents at a concentration of less than 5% based on the weight of the total concentration.

16. Composition according to claim 1 wherein the composition is a transparent composition.

17. Composition according to claim 1 wherein the composition is a non-transparent pearly composition and contains pearlizing agents at a concentration of 0.1 to 3% based on the weight of the total composition.

* * * * *